US011638905B2

(12) United States Patent
Raynal et al.

(10) Patent No.: US 11,638,905 B2
(45) Date of Patent: May 2, 2023

(54) COMPARTMENTALIZED OLIGOMERIZATION REACTOR

(71) Applicant: IFP Energies nouvelles, Rueil-Malmaison (FR)

(72) Inventors: Ludovic Raynal, Rueil-Malmaison (FR); Alexandre Vonner, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 279 days.

(21) Appl. No.: 16/884,934

(22) Filed: May 27, 2020

(65) Prior Publication Data

US 2020/0376460 A1    Dec. 3, 2020

(30) Foreign Application Priority Data

May 28, 2019  (FR) .................................... 19/05.669

(51) Int. Cl.
| | |
|---|---|
| *B01J 19/18* | (2006.01) |
| *B01J 10/00* | (2006.01) |
| *B01J 4/00* | (2006.01) |
| *B01J 19/00* | (2006.01) |
| *C07C 2/08* | (2006.01) |

(52) U.S. Cl.
CPC ........... *B01J 19/1868* (2013.01); *B01J 4/001* (2013.01); *B01J 4/008* (2013.01); *B01J 10/00* (2013.01); *B01J 19/0066* (2013.01); *B01J 2219/00256* (2013.01); *B01J 2219/185* (2013.01); *C07C 2/08* (2013.01)

(58) Field of Classification Search
CPC ............... B01J 19/1868; B01J 19/1862; B01J 19/1818; B01J 19/245; B01J 19/242; B01J 19/0066; B01J 10/00; B01J 4/001; B01J 4/008; B01J 2219/185; C07C 2/08
See application file for complete search history.

(56) References Cited

U.S. PATENT DOCUMENTS

| | | | | |
|---|---|---|---|---|
| 3,235,342 A | * | 2/1966 | Weber, Jr. ............. | C01B 25/265 422/224 |
| 2015/0231596 A1 | * | 8/2015 | Bushkov .............. | B01J 19/2425 422/129 |
| 2017/0081257 A1 | * | 3/2017 | Kreischer ............ | B01J 19/1818 |
| 2020/0001266 A1 | * | 1/2020 | Augier ........................ | B01J 8/22 |
| 2020/0094213 A1 | * | 3/2020 | Augier ................... | B01J 19/006 |

FOREIGN PATENT DOCUMENTS

| | | |
|---|---|---|
| DE | 102009039644 A1 | 3/2011 |
| FR | 3068620 A1 | 1/2019 |

OTHER PUBLICATIONS

Preliminary Search in corresponding FR1905669 dated Dec. 4, 2019 (pp. 1-7).

* cited by examiner

*Primary Examiner* — Lessanework Seifu
(74) *Attorney, Agent, or Firm* — Millen, White, Zelano and Branigan, P.C.; Harry B. Shubin

(57) ABSTRACT

The present invention relates to the field of gas/liquid reactors permitting the oligomerization of olefins to give linear olefins by homogeneous catalysis, comprising a reaction chamber and vertical internal means of compartmentalization.

13 Claims, 5 Drawing Sheets

[Fig 1]
Figure 1: Change in conversion as a function of the number of compartments and for two selectivity values 90 and 91%
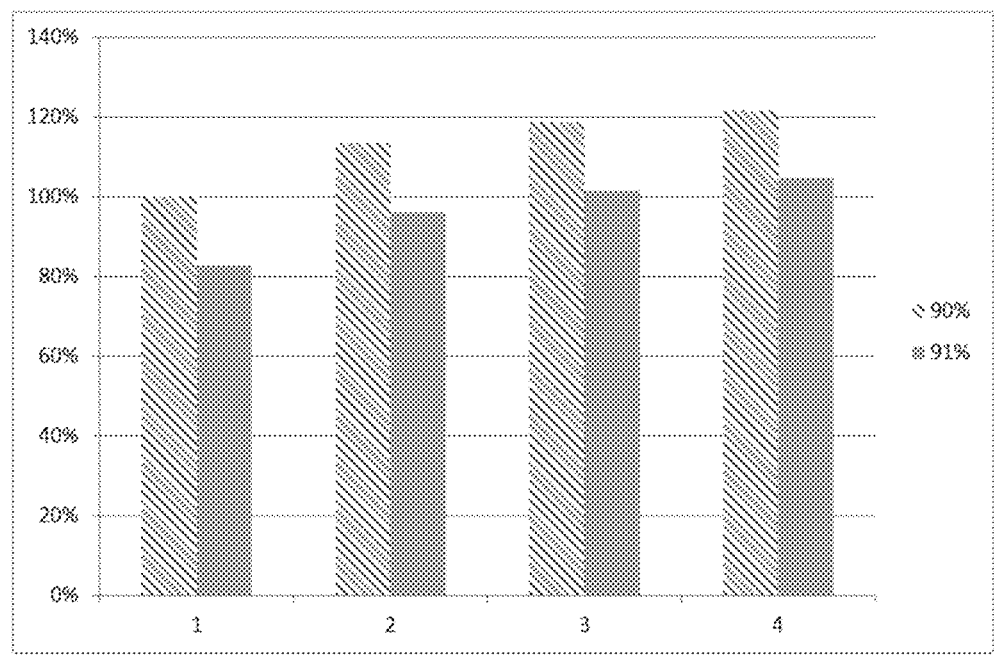

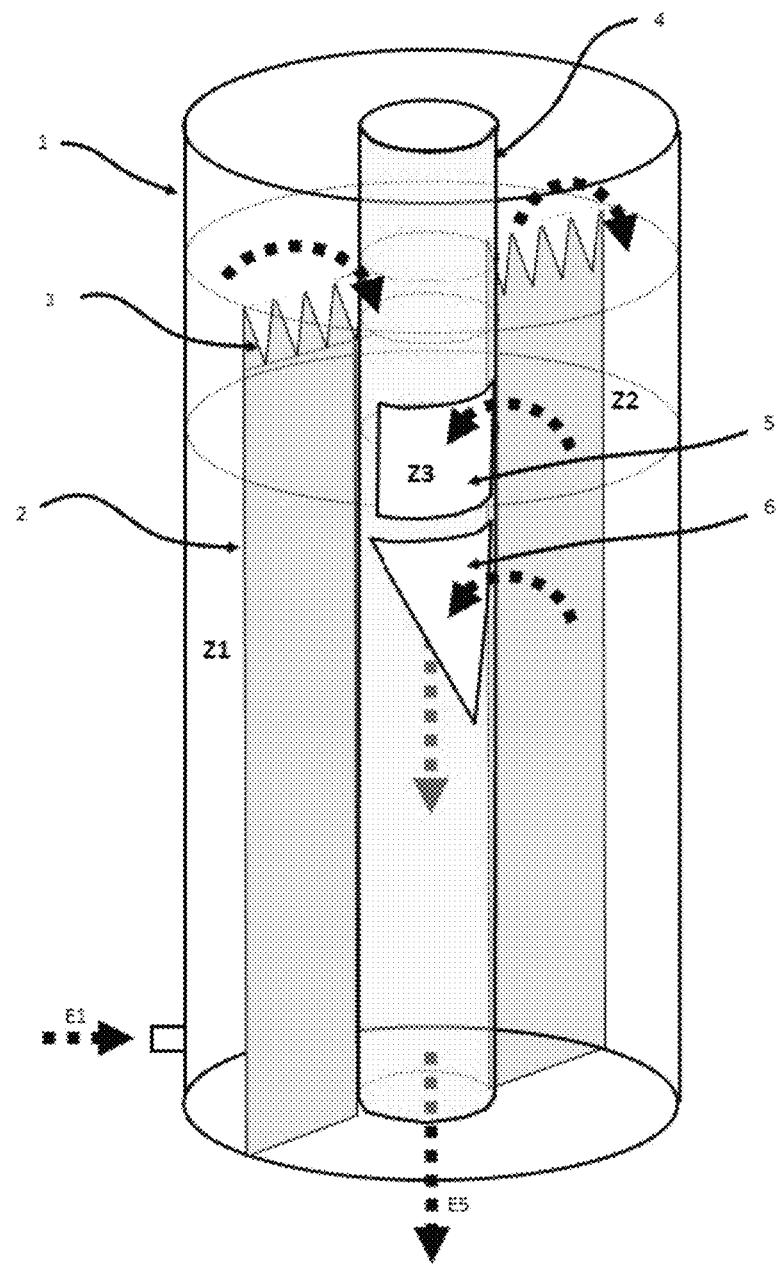
[Fig 2]

[Fig 3]
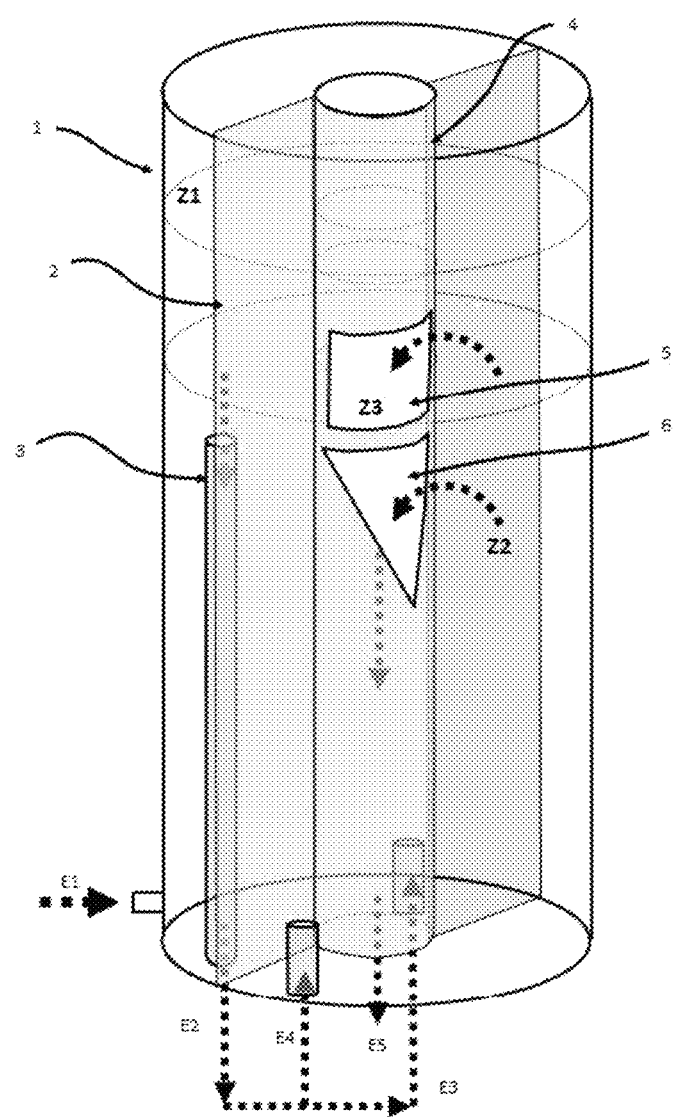

[Fig 4]
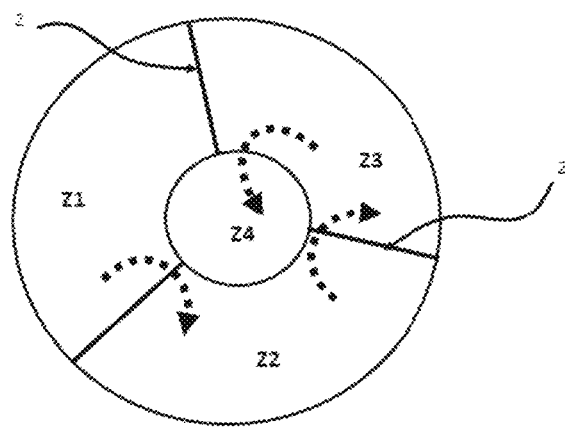
[Fig 5]
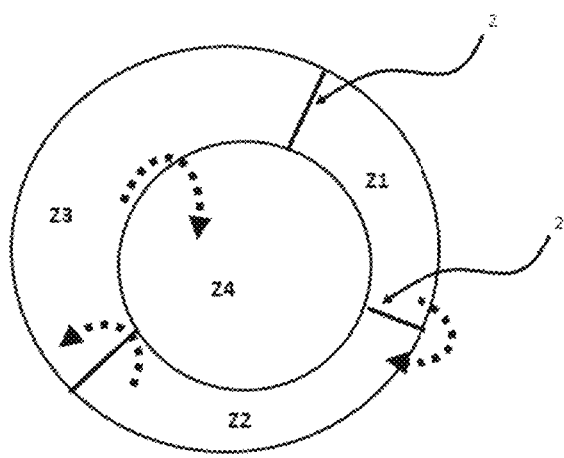

[Fig 6]
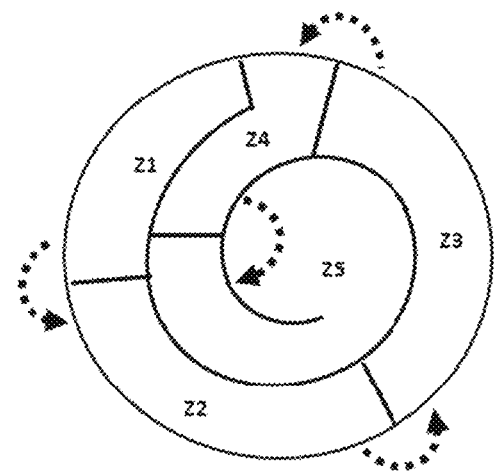

COMPARTMENTALIZED OLIGOMERIZATION REACTOR

TECHNICAL FIELD

The present invention relates to the field of gas/liquid reactors permitting the oligomerization of olefins to give linear olefins by homogeneous catalysis, comprising a reaction chamber and vertical internal means of compartmentalization.

The invention also relates to the use of the compartmentalized gas/liquid reactor in a process for oligomerization of ethylene to give linear alpha-olefins, such as but-1-ene, hex-1-ene or oct-1-ene, or a mixture of linear alpha-olefins.

The applicant has developed a novel reactor compartmentalized into n oligomerization zones. Surprisingly, the use of said reactor in a process for oligomerization of an olefinic feedstock, and in particular of ethylene, advantageously makes it possible to achieve higher levels of selectivity and conversion. In particular, the reactor according to the invention makes it possible to selectively obtain linear olefins, preferably alpha-olefins, such as but-1-ene, hex-1-ene and oct-1-ene.

Another advantage of the reactor according to the invention is to facilitate construction and thus limit the costs of implementation for the oligomerization of ethylene in n oligomerization zones compared to an implementation in a chain of several reactors.

SUBJECT MATTER OF THE INVENTION

The subject matter of the present invention is therefore a reactor for oligomerization of olefins by homogeneous catalysis, comprising
a reactor chamber (1) of elongate shape along the vertical axis;
a plurality of n oligomerization zones (Zn), which are delimited by internal compartmentalization walls (2, 4) arranged along the vertical axis of the chamber (1) and which are each able to contain a liquid part of catalytic activity and a gaseous part;
means for connecting the n oligomerization zones in series;
a means for introducing, into the first compartment Z1, a flow comprising an olefinic feedstock;
a means for withdrawing, from the final compartment Zn, an oligomerization effluent,
in which reactor
n is an integer between 2 and 10;
said internal compartmentalization walls are arranged in such a way as to delimit said n oligomerization zones (Zn) interconnected in series so as to be able to transfer a liquid phase of catalytic activity from a zone Zn-1 to an adjacent zone Zn by way of said connection means.

Preferably, the compartmentalization walls, being identical or different, are chosen from among flat plates, curved plates, cylindrical walls or helical plates.

Preferably, at least one internal compartmentalization wall extends over the entire length of the reactor, so as to prevent the passage of liquid between two adjacent oligomerization zones.

Preferably, the means of connection between the two adjacent oligomerization zones are outside the reactor chamber (1).

Preferably, the reactor additionally comprises internal connection means, so as to obtain a gravitational flow.

Preferably, the internal connection means are chosen from among orifices or recesses.

Preferably, the internal compartmentalization walls have a triangular and/or circular shape in their upper parts.

Preferably, the connection means of the upstream compartmentalization wall can be advantageously situated higher than the connection means of the adjacent downstream compartmentalization wall.

Preferably, the number n of oligomerization zones is between 2 and 8.

Preferably, the reactor chamber (1) has a height to width ratio (denoted H/W) of between 1 and 17.

Preferably, each oligomerization zone comprises one or more stirring means chosen from among a recirculation loop and a mechanical stirring means.

Preferably, each oligomerization zone comprises a recirculation loop in combination with at least one heat exchanger.

Preferably, one or more of the oligomerization zones Z2 to Zn comprises a means for introducing the olefinic feedstock.

Preferably, the final oligomerization zone Zn does not comprise a means for introducing the olefinic feedstock.

Preferably, the gas/liquid oligomerization reactor comprises a means for introducing the catalytic system into the first oligomerization zone Z1, said means being situated in the lower part, more particularly in the bottom of said first oligomerization zone Z1.

The present invention also relates to a process of oligomerization by homogeneous catalysis, using the reactor as defined above.

The various components of the reactor will be described with reference to all of the figures, each component retaining the same reference sign from one figure to another.

BRIEF DESCRIPTION OF THE DRAWINGS

FIG. 1 is a graph illustrating the change in the conversion of ethylene (ordinate) as a function of the number of oligomerization zones arranged in series in a reactor (abscissa) for hex-1-ene selectivities of 90% and 91%. The values are standardized by the reference value obtained for 1 reactor and a selectivity of 90%. The results shown in FIG. 1 were obtained by catalysis with chromium, as described in the patent FR 3 019 064 and illustrated in the examples.

FIG. 2 shows a schematic three-dimensional view of a gas/liquid oligomerization reactor according to the invention. The reactor has a reactor chamber 1, in which three oligomerization zones arranged in series and labelled Z1, Z2 and Z3 are delimited by internal compartmentalization walls 2 and 4. The wall 2 is a vertical flat plate, and the wall 4 is a cylindrical plate. The compartments Z1 and Z2 are connected by connection means 3 corresponding to recesses of triangular shape in the upper part of the internal wall 2. The compartments Z2 and Z3 are connected by connection means 5 and 6 corresponding to recesses of rectangular and triangular shape, respectively, in the upper part of the internal wall 4 and at a level below the connection means 3. The broken arrows represent the direction of flow of the liquid in the reactor between the oligomerization zones Z1 to Z3 connected in series. The broken arrows also represent the introduction of the olefinic feedstock E1 into the oligomerization zone Z1 by a means of introduction, and the withdrawal of the oligomerization effluent E5 from the final zone Z3 by a withdrawal means.

FIG. 3 shows a schematic three-dimensional view of another gas/liquid oligomerization reactor according to the invention. The reactor of FIG. 3 differs from that of FIG. 2 in that the internal compartmentalization walls 2 extend as far as the top of the reactor chamber, thereby delimiting oligomerization zones Z1 and Z2 isolated from each other. The oligomerization zones Z1 and Z2 are connected by external connection means. The olefinic feedstock E1 is introduced into the bottom of the oligomerization zone Z1, and the liquid part of the reactor is withdrawn in a flow E2. Said flow E2 is divided into two flows E3 and E4. The flow E4 is introduced into the oligomerization zone Z2. The flows E2 and E3 correspond to a recirculation loop of the oligomerization zone Z1 and make it possible to obtain good stirring of the liquid part of the zone Z1. The olefinic feedstock E1 is introduced into the oligomerization zone Z1 by a means of introduction, and the oligomerization effluent E5 is withdrawn from the final zone Z3 by a withdrawal means. The broken arrows represent the direction of circulation of the flows in the different oligomerization zones of the reactor.

FIG. 4 is a schematic plan view of a reactor according to the invention comprising four oligomerization zones connected in series, in which the zones Z1, Z2 and Z3 have the same dimensions. The zones Z1, Z2 and Z3 are delimited by flat internal compartmentalization walls 2. The zone Z4 is delimited by a cylindrical internal wall. The broken arrows represent the direction of flow of the liquid part from the zone Z1 to the zone Z2, from the zone Z2 to the zone Z3, and from the zone Z3 to the zone Z4.

FIG. 5 is another schematic plan view and shows an arrangement of the reactor that differs from FIG. 4 in that all the zones have different dimensions. In this particular case, the volume of the sections is gradually increased from Z1 to Z4 so as to promote an increase of the residence time in the zone as the oligomerization reaction proceeds.

FIG. 6 is another schematic plan view and shows an arrangement of the reactor in which 5 oligomerization zones are delimited by a combination of a helical plate and flat plates.

DEFINITIONS AND ABBREVIATIONS

Throughout the description, the terms or abbreviations below have the following meanings.

Oligomerization is understood to mean any addition reaction of a first olefin with a second olefin identical to or different from the first olefin. The olefin thus obtained is of the CnH2n type, where n is equal to or greater than 4.

Homogeneous catalysis is understood to mean catalysis in which the catalytic system is soluble or dissolved in the liquid part.

Alpha-olefin is understood to mean an olefin in which the double bond is located at the terminal position of the alkyl chain.

Catalytic system is understood to mean the mixture of at least one metal precursor, optionally of at least one activating agent, and optionally of at least one ligand, optionally in a solvent.

Lateral lower part of the reaction chamber is understood to mean a part of the shell of the reactor located in the bottom part and on the side.

The terms upstream and downstream, in the context of the invention, are used with reference to the circulation of the liquid fraction in the reactor.

Throughout the present text, spatial positioning terms such as "vertical", "horizontal", "upper" or "lower" are to be understood with a reactor disposed in a horizontal plane in its operating position, as is shown in FIGS. 1 and 2.

DETAILED DESCRIPTION OF THE INVENTION

It is specified that, throughout this description, the expression "between . . . and . . . " should be understood as including the limits mentioned.

Within the meaning of the present invention, the different embodiments presented can be used alone or in combination with one another, without any limit to the combinations when this is technically feasible.

A particular type of reactor according to the invention is a reactor composed of a single embodiment or of a combination of several embodiments as described below, where they are technically compatible.

Reactor

The present invention thus relates to a reactor, preferably a gas/liquid reactor, for oligomerization by homogeneous catalysis, comprising a reactor chamber (1) of elongate shape along the vertical axis;

a plurality of n oligomerization zones (Zn), which are delimited by internal compartmentalization walls (2, 4) arranged along the vertical axis of the chamber (1) and which are each able to contain a liquid part of catalytic activity and a gaseous part;

means for connecting the n oligomerization zones in series;

a means for introducing, into the first zone Z1, a flow comprising the olefinic feedstock;

a means for withdrawing, from the final zone Zn, an oligomerization effluent, in which reactor n is an integer between 2 and 10;

said internal compartmentalization walls are arranged in such a way as to delimit said n oligomerization zones (Zn) interconnected in series so as to be able to transfer a liquid phase of catalytic activity from a zone Zn-1 to an adjacent zone Zn by way of said connection means.

Preferably, the oligomerization reactor, preferably a gas/liquid oligomerization reactor, comprises a number n of oligomerization zones of between 2 and 8 and preferably of between 2 and 6, and n is preferably equal to 2, 3, 4 or 5.

The oligomerization zones according to the invention are connected in series and delimited along the vertical axis of the reactor in such a way as to define zones having liquid parts with concentrations of reagents, catalyzers and various products, making it possible, in all the oligomerization zones contained in the reaction chamber, to approach a hydrodynamic behaviour of a reactor of the plug-flow type. Another advantage of the reactor according to the invention is to obtain an arrangement of the plug-flow type in a single reactor, which greatly reduces the costs of implementation of the reactor.

For the final zone Zn of the cascade of oligomerization zones, the effluent withdrawn by the withdrawal means corresponds to the effluent obtained at the end of the oligomerization process and can be conveyed to a separation section in order to separate the linear olefins produced. Preferably, the withdrawal means is a pipe.

The reactor comprises a reactor chamber (1), preferably having a cylindrical wall.

Preferably, the reactor chamber (1) has a height to width ratio (denoted H/W) of between 1 and 17, preferably of between 1 and 8, and by preference between 2 and 6.

The oligomerization zones (Zn) delimited by the internal compartmentalization walls can be of identical size, increasing or decreasing in the direction of flow of the liquid fraction in the reactor, depending on the desired hydrodynamic behaviour.

Recirculation Loop

Advantageously, the gas/liquid oligomerization reactor comprises one or more stirring means in each oligomerization zone, chosen from among a recirculation loop and a mechanical stirring means. Said mechanical stirring means designates a stirring blade, a vane, or any other means known to a person skilled in the art.

In a preferred embodiment, the gas/liquid oligomerization reactor preferably comprises one recirculation loop per oligomerization zone. Each recirculation loop comprises at least one withdrawal means, preferably in the lower part of an oligomerization zone, preferably at the bottom, and a means of introduction, preferably in the upper part of an oligomerization zone.

The recirculation loop makes it possible to achieve good homogenization of the concentrations in the liquid part of an oligomerization zone of the reactor. Thus, the homogenization in each of the oligomerization zones Zn can be regulated independently of one another.

Preferably, each of the n oligomerization zones Zn of the reactor according to the invention comprises a recirculation loop.

The withdrawal is carried out by any means capable of carrying out the withdrawal, the withdrawal means preferably being a pipe, optionally in combination with a pump.

For each oligomerization zone comprising a recirculation loop, the withdrawal of liquid from a given oligomerization zone is preferably carried out starting from a point located below the point of introduction into said zone. For a given oligomerization zone comprising a recirculation loop, the withdrawal is preferably carried out in the lower part of the oligomerization zone. For each oligomerization zone comprising a recirculation loop, the introduction into said oligomerization zone is preferably carried out starting from a point located above the liquid withdrawal point. For a given oligomerization zone comprising a recirculation loop, the introduction is preferably carried out in the upper part of said zone.

In another embodiment, the introduction and the withdrawal are carried out all along the reactor via tubes provided with orifices, which may be cylindrical holes or slits, preferably spaced at regular intervals all along the introduction or withdrawal tube. The smallest characteristic dimension of the orifices (width of slit or diameter) is preferably greater than 2 mm, preferably greater than 5 mm, and by preference greater than 8 mm, in order to avoid any risk of clogging.

Any other type of injection or withdrawal is possible, the aim being to maintain an independent loop between each zone.

Advantageously, a recirculation loop additionally comprises a heat exchanger or several heat exchangers, so as to cool a liquid fraction in the recirculation loop.

The heat exchangers suitable for cooling the liquid fraction are chosen from any means known to a person skilled in the art.

Preferably, each oligomerization zone comprises a heat exchanger integrated in a recirculation loop. Preferably, each oligomerization zone has its own recirculation loop with its point of entry of liquid and its point of departure of liquid originating from said loop. The recirculation loop can advantageously be implemented by any necessary means known to a person skilled in the art, such as a pump for the withdrawal of the liquid fraction, a means capable of regulating the flow rate of the withdrawn liquid fraction, or also a pipe for bleeding off at least a portion of the withdrawn liquid fraction.

When the first oligomerization zone Z1 comprises a recirculation loop and a heat exchanger, the introduction of the cooled liquid in said zone Z1 is preferably carried out in the gaseous part or in the upper zone of the liquid part, by any means known to a person skilled in the art. The withdrawal is preferably carried out below the level of introduction of the olefinic feedstock, and preferably in the bottom of the oligomerization zone.

The withdrawal is advantageously carried out by any means capable of carrying out the withdrawal, notably by using a pump.

Advantageously, for an oligomerization zone of the reactor according to the invention, the liquid phase is preferably withdrawn by admission means under the control of the liquid level, so as to keep the latter constant. The admission means are any means well known to a person skilled in the art, such as a valve.

Internal Compartmentalization Walls

According to the invention, the gas/liquid reactor for oligomerization by homogeneous catalysis comprises compartmentalization walls for delimiting n oligomerization zones designated Zn in the reactor, thus making it possible to approach a hydrodynamic behaviour of a reactor of the plug-flow type, by virtue of the n oligomerization zones being arranged in series.

Preferably, the compartmentalization walls, being identical or different, are chosen from among flat plates, curved plates, cylindrical walls or helical plates.

In a first particular embodiment, the internal compartmentalization walls extend over the full height of the reactor, that is to say from the bottom to the top of the reactor, so as to prevent passage of liquid between two adjacent zones. Thus, the liquid parts of the compartments are isolated from one another, and the communication in series is provided by connection means situated outside the reactor chamber 1, called external connection means.

In a second particular embodiment, the communication in series between the oligomerization zones is provided by connection means located inside the reactor chamber. In this case, the internal connection means are advantageously orifices or recesses present on each of the internal compartmentalization walls in order to ensure the flow of the liquid, preferably by gravity, from an upstream zone to an adjacent downstream zone.

Preferably, whatever the embodiment, the upper gas phase is common to the different oligomerization zones.

Advantageously, when the reactor comprises internal connection means, said means can be obtained by special recess geometries in the internal compartmentalization walls, so as to have a flow of the liquid in series, preferably by gravitational flow, from an oligomerization zone Z1 to an adjacent oligomerization zone Z2 and from the zone Z2 to an adjacent zone Z3 as far as the final oligomerization zone Zn.

Without limitation, the internal compartmentalization walls can have a triangular or circular shape in their upper part, so as to have a cross section of passage that increases as the liquid level rises during the operation of the reactor. An advantage of this type of geometry is to permit flexibility in the operation of the reactor, notably as regards the adaptation of the flow rates/of the residence time, while maintaining a stable level of liquid in the compartment.

When the oligomerization zones Zn are connected by gravitational flow, the connection means of the upstream compartmentalization wall can be advantageously situated higher than the connection means of the adjacent downstream compartmentalization wall.

The gas/liquid oligomerization reactor can comprise a combination of compartmentalization walls according to the first and second embodiments. Said reactor then comprises a combination of internal and external connection means.

In addition, the compartmentalization walls can be provided with openings, such as perforations, orifices of triangular, circular, square or rectangular shape, preferably at the reactor bottom, in such a way as to better distribute the liquid from an upstream oligomerization zone to the adjacent downstream oligomerization zone in the direction of flow. Preferably, said orifices can be partially or wholly on the upper part of the compartmentalization walls so as to impose a gravitational flow. Advantageously, when the openings are situated at the reactor bottom, they also make it easier to empty the entire reactor chamber, for example during shutdown phases and during maintenance operations.

In a particular embodiment, the external connection means of the oligomerization zones Z2 to Zn (hence with the exception of the first oligomerization zone of the reactor) are liquid supply means for introducing part of a liquid fraction withdrawn from the upstream oligomerization zone Zn-1 to the adjacent downstream oligomerization zone Zn. These supply means can be a pipe directly supplying the oligomerization zone Zn in one embodiment, or a pipe connecting the recirculation loop of the oligomerization zone Zn-1 directly to the adjacent oligomerization zone Zn, or a pipe connecting the recirculation loop of the oligomerization zone Zn-1 to the recirculation loop of said adjacent oligomerization zone Zn.

Preferably, the means for withdrawing the liquid part in the final oligomerization zone Zn of the reactor is a pipe. The liquid fraction withdrawn via said pipe corresponds to the effluent of the oligomerization process used in the reactor according to the invention.

One advantage of the present invention is thus that of making it possible to achieve selectivities for linear olefins, and preferably for linear alpha-olefins, which are superior to those achieved with a reactor according to the prior art comprising only a single reaction chamber, this being obtained while retaining a high level of conversion into linear olefins.

Means for Introduction of the Olefinic Feedstock

According to the invention, the gas/liquid oligomerization reactor comprises a means for introduction of the olefinic feedstock into the first oligomerization zone Z1, said means preferably being located in the lower part of the zone Z1 of the reactor, more particularly in the bottom of said zone Z1.

Advantageously, one or more of the oligomerization zones Z2 to Zn can also comprise a means for introduction of the olefinic feedstock. In a particular embodiment, one or more oligomerization zones Z2 to Zn-1 can comprise a means for introduction of the olefinic feedstock, that is to say the final oligomerization zone Zn does not comprise a means for introduction of the olefinic feedstock.

Preferably, the means for introduction of the olefinic feedstock is chosen from a pipe, a network of pipes, a multitubular distributor, a perforated plate or any other means known to a person skilled in the art.

Preferably, a gas distributor, which is a device making it possible to disperse the gaseous olefinic feedstock uniformly over the entire liquid section of an oligomerization zone, is positioned at the end of said introduction means of said feedstock within an oligomerization zone of the reactor. Said device comprises a network of perforated pipes, the diameter of the orifices of which is between 1 and 12 mm, preferably between 3 and 10 mm, in order to form ethylene bubbles of millimetric size in the liquid.

Said gas/liquid oligomerization reactor can also comprise a means for introduction of the catalytic system in the first oligomerization zone Z1, said means being located in the lower part, more particularly in the bottom of said zone Z1. Advantageously, one or more of the oligomerization zones Z2 to Zn can also comprise a means for introduction of the catalytic system. According to an alternative embodiment, the catalytic system is introduced into the recirculation loop of an oligomerization zone.

The distribution of the catalytic activity in the different oligomerization zones Z1 to Zn of the reactor according to the invention is determined by the quantities of catalytic systems that are introduced into each of the oligomerization zones.

Withdrawal Means

According to the invention, the gas/liquid reactor for oligomerization by homogeneous catalysis comprises a means for withdrawing an oligomerization effluent from the final oligomerization zone Zn.

Thus, in the reactor according to the invention, the combination of the means for introduction of the olefinic feedstock in the first oligomerization zone Z1, of the withdrawal means in the final oligomerization zone Zn and of the means for connection in series of the oligomerization zones makes it possible to dictate the direction of flow from zone Z1 to zone Zn, thus making it possible to approach the hydrodynamic behaviour of a reactor of the plug-flow type.

Process Using the Reactor According to the Invention

The invention also relates to the process of oligomerization using the reactor according to the present invention.

The process of oligomerization using the reactor according to the invention makes it possible to obtain linear olefins and in particular linear alpha-olefins by bringing olefin(s) and a catalytic system into contact, optionally in the presence of an additive and/or of a solvent, and by the use of said gas/liquid oligomerization reactor according to the invention.

Any homogeneous catalytic system known to a person skilled in the art and capable of being employed in the oligomerization processes, in particular in the dimerization, trimerization or tetramerization processes, comes within the field of the invention. Said catalytic systems and also the implementations thereof are described in particular in the applications FR 2 984 311, FR 2 552 079, FR 3 019 064, FR 3 023 183, FR 3 042 989 or else in the application FR 3 045 414. Preferably, the catalytic systems are based on nickel, titanium or chromium.

The olefinic feedstock is preferably a linear olefin comprising between 2 and 10 carbon atoms; the olefinic feedstock is preferably ethylene.

The oligomerization process is carried out at a pressure between 1.0 and 10.0 MPa, preferably between 2.0 and 8.0 MPa, more preferably between 4.0 and 8.0 MPa and more particularly between 6.0 and 8.0 MPa. The temperature is between 0° C. and 200° C., preferably between 30° C. and 180° C., more preferably between 30° C. and 150° C. and more preferably still between 40° C. and 140° C.

The residence time of the reaction medium in the reactor according to the invention is, on average, between 2 and 400 minutes, preferentially between 20 and 150 minutes, preferably between 30 and 120 minutes. The residence time of the reaction medium within each compartment is, on average, between 1 and 30 minutes, preferably between 5 and 20 minutes and more preferably still between 5 and 15 minutes.

The olefinic feedstock is preferably introduced by dispersion in the liquid part of the first oligomerization zone Z1, preferably in the lower part of the compartmentalized gas/liquid reactor, more preferably in the compartment Z1 and more particularly in the bottom.

The olefinic feedstock can be introduced into each oligomerization zone of the gas/liquid reactor according to the invention, preferably exclusively into the first oligomerization zone. More particularly, when the olefin is introduced into an oligomerization zone, the introduction is carried out in the lower part of said zone.

In one embodiment, the olefin can be introduced in one or more recirculation loops.

Preferably, the linear olefins that are obtained by the process using the reactor according to the invention comprise from 4 to 12 carbon atoms. Very preferably, the linear olefins obtained are linear alpha-olefins, preferably but-1-ene, hex-1-ene or oct-1-ene.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 19/05.669, filed May 28, 2019, are incorporated by reference herein.

The following examples illustrate the invention without limiting the scope thereof.

EXAMPLES

In the examples below, the means for introduction of the feedstock E1, for withdrawal of the effluent E5 and for connections are as shown in FIG. 2. When several zones are delimited by flat internal compartmentalization walls, the connection means are then as shown in FIG. 2 for flat internal walls 2.

Example 1 (According to the Invention Corresponding to a Reactor as Per FIG. 2, with an Arrangement of the Oligomerization Zones as Per FIG. 4

The example uses an ethylene oligomerization reactor comprising four oligomerization zones, which are of identical volume and are arranged as per FIG. 4. The catalytic system introduced into each compartment of the reactor is a chromium-based catalytic system with a content of 4 ppm of chromium, as described in the patent FR 3 019 064, in the presence of a solvent, namely cyclohexane.

The reaction volume of each of the oligomerization zones is 36.7 $m^3$. Said zones are all operated at a temperature of 135° C. and a pressure of 6.0 MPa.

The overall residence time in the reactor is 21.1 min.

The volumetric productivity of this reaction device is 170 kg of alpha-olefins produced per hour and per $m^3$ of total reaction volume.

The performance qualities of the reactor according to the invention make it possible to convert 49.07% of the injected ethylene, for a content by weight of solvent (2.7), and to achieve a selectivity of 91.04% for the hex-1-ene, which illustrates the benefit of a reactor according to the invention.

Example 2 (According to the Invention Corresponding to a Reactor as Per FIG. 2, with an Arrangement of the Oligomerization Zones as Per FIG. 5

The example uses an ethylene oligomerization reactor comprising four oligomerization zones which are of increasing volume in the direction of flow of the liquid part and which are arranged as per FIG. 5. In contrast to the case treated in example 1, the catalytic system is introduced only into the first compartment. This catalytic system is a chromium-based catalytic system with a content of 4 ppm of chromium, as described in the patent FR 3 019 064, and is introduced in the presence of a solvent, namely cyclohexane.

The reaction volumes of the oligomerization zones are 36.2 $m^3$, 43.8 $m^3$, 55.5 $m^3$ and 73.2 $m^3$. Said zones are all operated at a temperature of 135° C. and a pressure of 6.0 MPa.

The overall residence time in the reactor is 30.1 min.

The volumetric productivity of this reaction device is 120 kg of alpha-olefins produced per hour and per $m^3$ of total reaction volume.

The performance qualities of the reactor according to example 2 make it possible, for the same conversion of injected ethylene (49.07%) and for the same content by weight of solvent (2.7), to achieve a selectivity for hex-1-ene that is identical to the preceding case (91.04%), with simplified use by virtue of the existence of a single injection of the catalytic system into the reactor.

Example 3 (According to the Invention Corresponding to a Reactor as Per FIG. 2, with Increasing Volumes of the Oligomerization Zones The example uses an ethylene oligomerization reactor comprising three oligomerization zones which are of increasing volume in the direction of flow of the liquid part, and in which only the first two zones Z1 and Z2 have gaseous injection of ethylene in the bottom of each of said zones Z1 and Z2. The catalytic system introduced exclusively into the first compartment is a chromium-based catalytic system with a content of 4 ppm of chromium, as described in the patent FR 3 019 064, in the presence of a solvent, namely cyclohexane.

The reaction volumes of the oligomerization zones are 52.7 $m^3$, 66.0 $m^3$ and 89.2 $m^3$. Said zones are all operated at a temperature of 135° C. and a pressure of 6.0 MPa.

The overall residence time in the reactor is 36.5 min.

The volumetric productivity of this reaction device is 120 kg of alpha-olefins produced per hour and per $m^3$ of total reaction volume.

The performance qualities of this reaction device according to the invention make it possible, at a selectivity for hex-1-ene of 89.78%, to increase the conversion to 63.36% of the ethylene injected, for a solvent content of (2.8), and allow simplified use in a single reactor, with an injection of the catalytic system at a single location.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A reactor suitable for oligomerization by homogeneous catalysis, comprising
   a reactor chamber (1) of elongate shape along the vertical axis;
   a plurality of n oligomerization zones (Zn), which are delimited by internal compartmentalization walls arranged along the vertical axis of the chamber (1) and which are each able to contain a liquid part of catalytic activity and a gaseous part;
   connection of the n oligomerization zones in series;
   an inlet introducing, into each compartment Z1 to Zn-1, a flow comprising an olefinic feedstock;
   an outlet withdrawing, from the final compartment Zn, an oligomerization effluent, in which reactor
   n is an integer equal to 3;
   said internal compartmentalization walls are flat plates and a cylindrical wall arranged in such a way as to delimit said n oligomerization zones (Zn) interconnected in series so as to be able to transfer a liquid phase of catalytic activity from a zone Zn-1 to an adjacent zone Zn by way of said connection.

2. The reactor according to claim 1, in which at least one internal compartmentalization wall extends over the entire length of the reactor, so as to prevent the passage of liquid between two adjacent oligomerization zones.

3. The reactor according to claim 2, in which the connection between the two adjacent oligomerization zones are outside the reactor chamber (1).

4. The reactor according to claim 1, comprising internal connections obtaining a gravitational flow.

5. The reactor according to claim 4, in which the internal connections are orifices or recesses.

6. The reactor according to claim 4, in which the internal compartmentalization walls have a triangular and/or circular shape in their upper parts.

7. The reactor according to claim 4, in which the connection of the upstream compartmentalization wall can be advantageously situated higher than the connection of the adjacent downstream compartmentalization wall.

8. The reactor according to claim 1, in which the reactor chamber (1) has a height to width ratio (denoted H/W) of 1 to 17.

9. The reactor according to claim 1, in which each oligomerization zone comprises one or more stirrers which are a recirculation loop and/or a mechanical stirrer.

10. The reactor according to claim 9, in which each oligomerization zone comprises a recirculation loop in combination with at least one heat exchanger.

11. The reactor according to claim 1, in which one or more of the oligomerization zones Z2 to Zn comprises an inlet introducing the olefinic feedstock.

12. The reactor according to claim 1, in which the final oligomerization zone Zn does not comprise an inlet introducing the olefinic feedstock.

13. A process of oligomerization by homogeneous catalysis, using the reactor according to claim 1.

* * * * *